US008652205B2

(12) United States Patent
Hong et al.

(10) Patent No.: US 8,652,205 B2
(45) Date of Patent: Feb. 18, 2014

(54) PHASE-SHIFTED CENTER-DISTANCE DIFFRACTIVE DESIGN FOR OCULAR IMPLANT

(75) Inventors: Xin Hong, Fort Worth, TX (US); Mutlu Karakelle, Fort Worth, TX (US); Xioaxioa Zhang, Fort Worth, TX (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/910,446

(22) Filed: Oct. 22, 2010

(65) Prior Publication Data
US 2011/0098811 A1 Apr. 28, 2011

Related U.S. Application Data

(60) Provisional application No. 61/254,938, filed on Oct. 26, 2009.

(51) Int. Cl.
*A61F 2/16* (2006.01)
(52) U.S. Cl.
USPC .......... 623/6.3; 623/6.27; 623/6.28; 623/6.29
(58) Field of Classification Search
USPC ................................. 623/6.27–6.31
See application file for complete search history.

(56) References Cited

U.S. PATENT DOCUMENTS

| | | | |
|---|---|---|---|
| 4,162,122 A | 7/1979 | Cohen | |
| 4,210,391 A | 7/1980 | Cohen | |
| 4,338,005 A | 7/1982 | Cohen | |
| 4,340,283 A | 7/1982 | Cohen | |
| 4,637,697 A | 1/1987 | Freeman | |
| 4,641,934 A | 2/1987 | Freeman | |
| 4,642,112 A | 2/1987 | Freeman | |
| 4,655,565 A | 4/1987 | Freeman | |
| 4,881,804 A | 11/1989 | Cohen | |
| 4,881,805 A | 11/1989 | Cohen | |
| 4,888,012 A | 12/1989 | Horn et al. | |
| 4,995,714 A * | 2/1991 | Cohen | 351/159.41 |
| 4,995,715 A | 2/1991 | Cohen | |
| 5,017,000 A | 5/1991 | Cohen | |
| 5,054,905 A | 10/1991 | Cohen | |
| 5,056,908 A | 10/1991 | Cohen | |
| 5,076,684 A | 12/1991 | Simpson et al. | |
| 5,096,285 A | 3/1992 | Silberman | |
| 5,116,111 A | 5/1992 | Simpson et al. | |
| 5,117,306 A | 5/1992 | Cohen | |
| 5,120,120 A | 6/1992 | Cohen | |
| 5,121,979 A | 6/1992 | Cohen | |

(Continued)

FOREIGN PATENT DOCUMENTS

| | | |
|---|---|---|
| CA | 2602507 A1 | 9/2006 |
| EP | 0742462 A2 | 11/1996 |

(Continued)

*Primary Examiner* — David H Willse
*Assistant Examiner* — Tiffany Shipmon
(74) *Attorney, Agent, or Firm* — Jonathan E. Prejean

(57) ABSTRACT

A diffractive multifocal design for ocular implant is provided. This ocular implant includes a diffractive multifocal intraocular lens (IOL) and a number of haptics. The diffractive multifocal IOL passes optical energy to distance, intermediate and near foci. The haptics mechanically couple to the diffractive multifocal IOL in order to position and secure the diffractive multifocal IOL within the eye. The diffractive multifocal IOL may include both a diffractive region and a refractive region, the diffractive multifocal IOL operable to phase shift optical energy such that constructive interference occurs within the diffractive region and the refractive region.

7 Claims, 9 Drawing Sheets

(56) References Cited

U.S. PATENT DOCUMENTS

| | | |
|---|---|---|
| 5,121,980 A | 6/1992 | Cohen |
| 5,129,718 A | 7/1992 | Futhey et al. |
| 5,144,483 A | 9/1992 | Cohen |
| 5,217,489 A | 6/1993 | Van Noy et al. |
| 5,257,132 A | 10/1993 | Ceglio et al. |
| 5,470,932 A | 11/1995 | Jinkerson |
| 5,528,322 A | 6/1996 | Jinkerson |
| 5,543,504 A | 8/1996 | Jinkerson |
| 5,662,707 A | 9/1997 | Jinkerson |
| 5,699,142 A | 12/1997 | Lee et al. |
| 5,800,532 A | 9/1998 | Lieberman |
| 5,895,422 A | 4/1999 | Hauber |
| 6,432,246 B1 | 8/2002 | Blake |
| 6,536,899 B1 | 3/2003 | Fiala |
| 6,596,026 B1 | 7/2003 | Gross et al. |
| 6,599,317 B1 | 7/2003 | Weinschenk, III et al. |
| 6,638,305 B2 | 10/2003 | Laguette |
| 6,685,315 B1 | 2/2004 | De Carle |
| 6,695,881 B2 | 2/2004 | Peng et al. |
| 6,800,091 B2 | 10/2004 | Callahan et al. |
| 6,923,540 B2 | 8/2005 | Ye et al. |
| 6,951,391 B2 | 10/2005 | Morris et al. |
| 6,969,403 B2 | 11/2005 | Peng et al. |
| 7,073,906 B1 | 7/2006 | Portney |
| 7,150,760 B2 | 12/2006 | Zhang |
| 7,156,516 B2 | 1/2007 | Morris et al. |
| 7,188,949 B2 | 3/2007 | Bandhauer et al. |
| 7,322,695 B2 | 1/2008 | Wooley et al. |
| 7,350,916 B2 | 4/2008 | Hong et al. |
| 7,441,894 B2 | 10/2008 | Zhang et al. |
| 7,481,532 B2 | 1/2009 | Hong et al. |
| 7,572,007 B2 | 8/2009 | Simpson |
| 7,896,916 B2 | 3/2011 | Piers et al. |
| 2003/0014107 A1 | 1/2003 | Reynard |
| 2003/0065387 A1* | 4/2003 | Callahan et al. ............. 623/6.25 |
| 2004/0252274 A1* | 12/2004 | Morris et al. ................. 351/168 |
| 2006/0066808 A1 | 3/2006 | Blum et al. |
| 2006/0116764 A1* | 6/2006 | Simpson ...................... 623/6.23 |
| 2007/0171362 A1 | 7/2007 | Simpson et al. |
| 2009/0088840 A1 | 4/2009 | Simpson et al. |
| 2009/0187242 A1 | 7/2009 | Weeber et al. |

FOREIGN PATENT DOCUMENTS

| | | |
|---|---|---|
| EP | 2045648 A1 | 4/2009 |
| WO | 97/44689 A1 | 11/1997 |
| WO | 99/28769 A1 | 6/1999 |
| WO | 2006/023404 A2 | 3/2006 |
| WO | 2006/023404 A3 | 3/2006 |
| WO | 2006/047698 A1 | 5/2006 |
| WO | 2006/060480 A2 | 6/2006 |
| WO | 2010/059764 A1 | 5/2010 |
| WO | 2010/144315 A1 | 12/2010 |
| WO | 2010/144317 A1 | 12/2010 |

* cited by examiner

PHASE-SHIFTED CENTER-DISTANCE DIFFRACTIVE DESIGN FOR OCULAR IMPLANT

This application claims priority to U.S. Provisional Application Ser. No. 61/254,938 filed on Oct. 26, 2009.

TECHNICAL FIELD OF THE INVENTION

The present invention relates generally to multifocal ophthalmic lenses, and, more particularly, to multifocal intraocular lenses that can provide refractive and diffractive optical focusing powers.

BACKGROUND OF THE INVENTION

The human eye in its simplest terms functions to provide vision by transmitting light through a clear outer portion called the cornea, and focusing the image by way of a lens onto a retina. The quality of the focused image depends on many factors including the size and shape of the eye, and the transparency of the cornea and lens. Age and/or disease often cause the lens to become less transparent. Thus, vision deteriorates because of the diminished light which can be transmitted to the retina. This deficiency in the lens of the eye is medically known as a cataract.

Intraocular lenses (IOLs) are routinely implanted in patients' eyes during cataract surgery to replace a natural crystalline lens. Some IOLs employ diffractive structures to provide a patient with not only a far-focus power but also a near-focus power. In other words, such multifocal IOLs provide the patient with a degree of accommodation (sometimes referred to as "pseudo-accommodation"). Although patients having such IOLs generally enjoy the versatile focusing properties of these lenses, a small percentage make observations about the quality of their intermediate vision.

Various multifocal ophthalmic lens designs generally fall into one of two categories, refractive lenses and diffractive lenses. Diffractive lenses use nearly periodic microscopic structures on the lens to diffract light into several directions simultaneously. This is similar to a diffraction grating and the multiple diffraction orders focus the light into various images corresponding to different focal lengths of the lens. Diffractive multifocal contact lenses and IOLs are more fully discussed in U.S. Pat. Nos. 4,162,122, 4,210,391, 4,338,005, 4,340,283, 4,995,714, 4,995,715, 4,881,804, 4,881,805, 5,017,000, 5,054,905, 5,056,908, 5,120,120, 5,121,979, 5,121,980, 5,144,483, 5,117,306 (Cohen), U.S. Pat. Nos. 5,076,684, 5,116,111 (Simpson, et al.), U.S. Pat. No. 5,129,718 (Futhey, et al.) and U.S. Pat. Nos. 4,637,697, 4,641,934 and 4,655,565 (Freeman), the entire contents of which are incorporated herein by reference.

While a diffractive IOL may have a number of focal lengths, generally, IOLs with only two focal lengths (far and near) are the most common. As with any simultaneous vision multifocal lens, a defocused image (or images) is superimposed on the focused component because of the second lens power, but the defocused image is rarely observed by the user, who concentrates on the detail of interest.

Accordingly, there is a need for enhanced ophthalmic lenses for correcting vision, and more particularly, for such lenses that can be employed to compensate for the lost optical power of a removed natural lens. In particular, a need exists for an IOL with the ability to restore vision across a range of object distances following removal of a natural lens.

SUMMARY OF THE INVENTION

Embodiments of the present disclosure provide an improved diffractive multifocal design for ocular implant. This ocular implant includes a diffractive multifocal intraocular lens (IOL) and a number of haptics. The diffractive multifocal IOL passes optical energy in distance, intermediate and near conditions. The haptics mechanically couple to the diffractive multifocal IOL in order to position and secure the diffractive multifocal IOL within the eye. The diffractive multifocal IOL may include both a diffractive region and a refractive region. The diffractive region may be a central region or optic zone of the lens that includes concentric steps of gradually varying step heights in order to allocate energy based on lighting conditions and activity in order to create a full range of quality vision, i.e. near, intermediate and distant for the patient. This allows conditions where the natural lens of the eye must be replaced to be corrected.

Other embodiments of the present disclosure provide a method to correct for visual impairment of aphakia. In one embodiment this involves removing a natural lens from an eye when the lens may be diseased or damaged through accident. Next a diffractive multifocal IOL may be inserted within the eye and then secured and positioned with a number of haptics. The diffractive region of the diffractive multifocal IOL may simultaneously pass optical energy to distant, intermediate and near focal points in bright optical conditions while the outer refractive region may pass optical energy to distance vision in dim optical conditions. Yet another embodiment of the present disclosure provides a method to correct visual impairment. This method involves passing optical energy to the retina wherein the optical energy may be imaged. This optical energy is passed with a diffractive multifocal IOL typically located within the eye and used to replace the natural lens. The diffractive multifocal IOL passes optical energy in distance, intermediate and near conditions. The diffractive multifocal IOL can have a central diffractive region and an outer refractive region.

Embodiments of the present disclosure allow patients having visual impairment to have clear distance vision at smaller pupil conditions, i.e. photopic conditions, and have improved vision at larger pupil, i.e. mesopic conditions.

Other advantages of the present disclosure will become more apparent to one skilled in the art upon reading and understanding the detailed description of the preferred embodiments described herein with reference to the following drawings.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

DETAILED DESCRIPTION OF THE INVENTION

Preferred embodiments of the present disclosure are illustrated in the FIGs., like numerals being used to refer to like and corresponding parts of the various drawings.

An improved diffractive multifocal design for ocular implant is provided. This ocular implant includes a diffractive multifocal intraocular lens (IOL) and a number of haptics. The diffractive multifocal IOL passes optical energy in distance, intermediate and near conditions. The haptics mechanically couple to the diffractive multifocal IOL in order to position and secure the diffractive multifocal IOL within the eye. The diffractive multifocal IOL may include both a diffractive region and a refractive region, the diffractive multifocal IOL operable to phase shift optical energy such that constructive interference occurs within the diffractive region and the refractive region.

Figure 1:
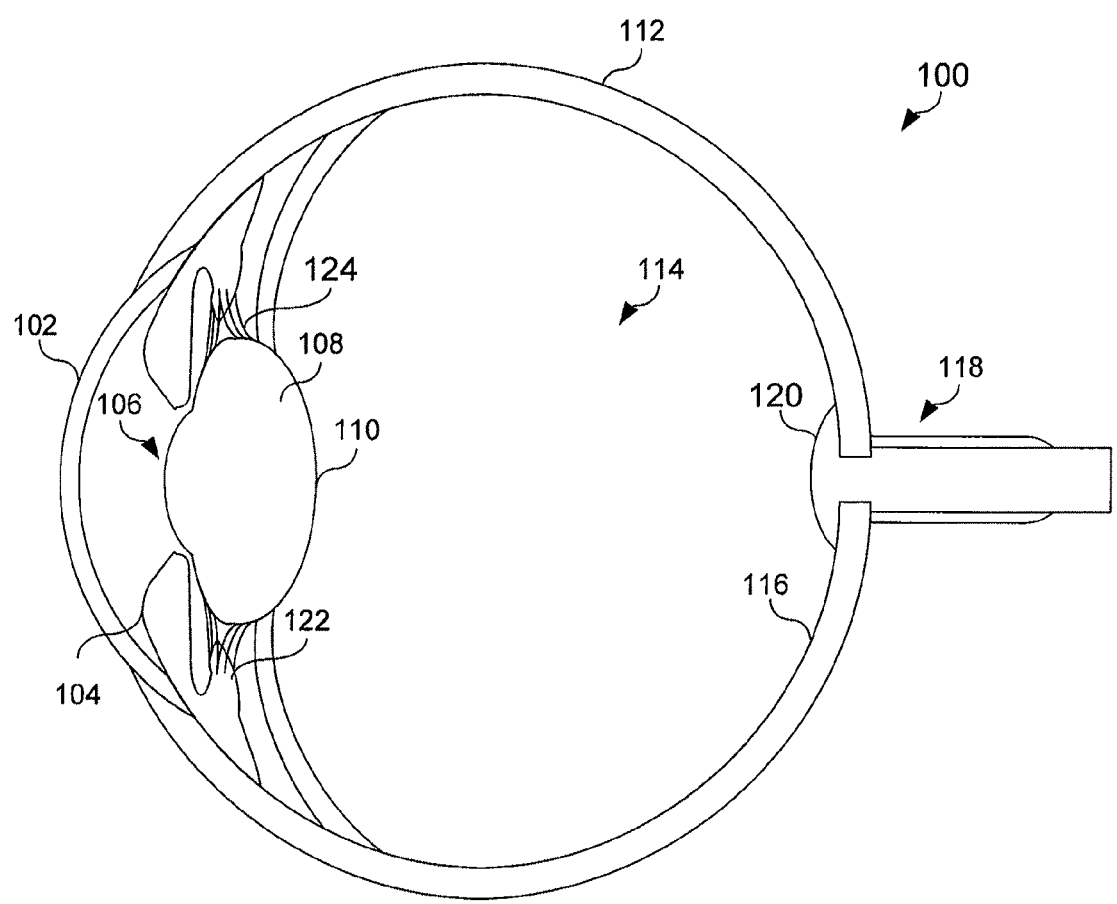
FIG. 1 illustrates the anatomy of the eye in which depicts an diffractive IOL in accordance with embodiments of the present disclosure may be placed.

Sight is, by far, one of our most valuable senses. Without our vision, everyday tasks like driving and reading books would be impossible. Our eyes are complex machines that deliver a clear picture of the world around us—communicating the simplest of colors, shapes and textures. FIG. 1 illustrates the anatomy of the eye into which the improved diffractive multifocal design for ocular implant provided by the present disclosure may be placed. Eye 100 includes cornea 102, iris 104, pupil 106, lens 108, lens capsule 110, zonules, ciliary body, sclera 112, vitreous gel 114, retina 116, macula, and optic nerve 120. Cornea 102 is a clear, dome-shaped structure on the surface of the eye acts as a window, letting light into the eye. Iris 104 is the colored part of the eye, called the iris, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The Ciliary body is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula is the area in the back of the eye that contains functions for seeing fine detail. Optic nerve 118 connects and transmits signals from the eye to the brain.

Figure 2A:
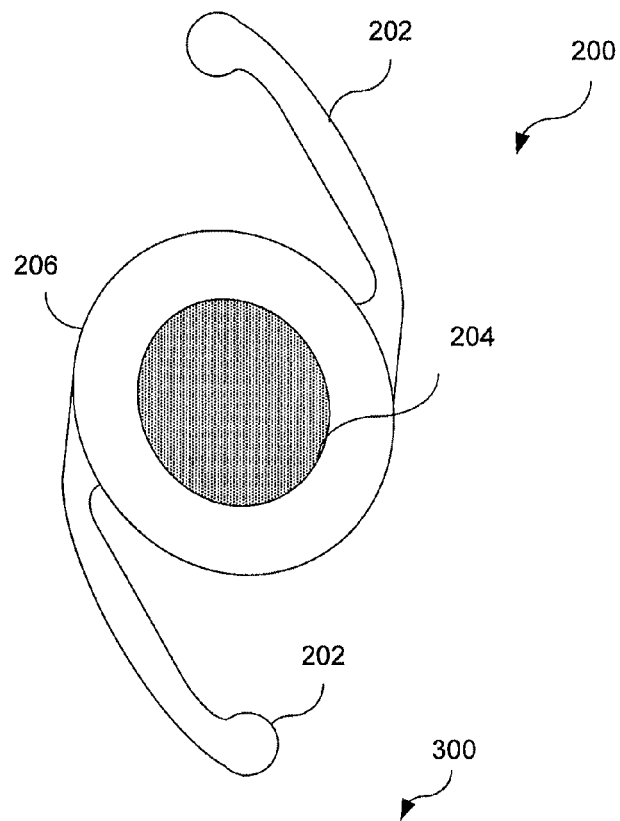
FIG. 2 depicts a diffractive IOL in accordance with embodiments of the present disclosure.
Figure 2B:
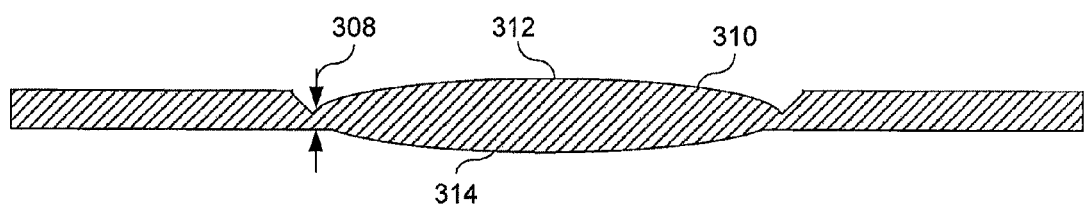

FIG. 2 depicts a diffractive IOL in accordance with embodiments of the present disclosure. Diffractive Optic IOL 200 provided is an artificial lens implanted in the eye to restore vision after a natural lens has been removed. The need for the IOL may be due to cataract, disease or accidents. The lens of the IOL may be convex on both sides (biconvex) and made of a soft plastic that can be folded prior to insertion, allowing placement through an incision smaller than the optic diameter of the lens. After surgical insertion into the eye, the lens gently unfolds to restore vision. The supporting arms (haptics) 202 provide for proper positioning of the IOL within the eye.

Diffractive Optic IOL 200 may be positioned in the posterior chamber of the eye, replacing the natural lens. This position allows Diffractive Optic IOL 200 to correct the visual impairment of aphakia (absence of the natural lens). Diffractive Optic IOL 200 may have a biconvex optic that is shaped using a process called apodized diffraction to provide increased depth of focus. The Diffractive Optic IOL 200 may be used in adult patients with and without presbyopia, who desire near, intermediate and distance vision with increased independence from glasses following cataract surgery. Diffractive Optic IOL 200 provides good near, intermediate and distance vision with increased independence from glasses in patients who have undergone cataract surgery. Diffractive Optic IOL 2 delivers quality vision for various lighting situations. In brightly lit conditions, the central diffractive portion 204 sends light waves simultaneously to distant, intermediate and near focal points, while, in dimly lit conditions, the surrounding refractive area 206 sends greater energy to distance vision.

Figure 3:
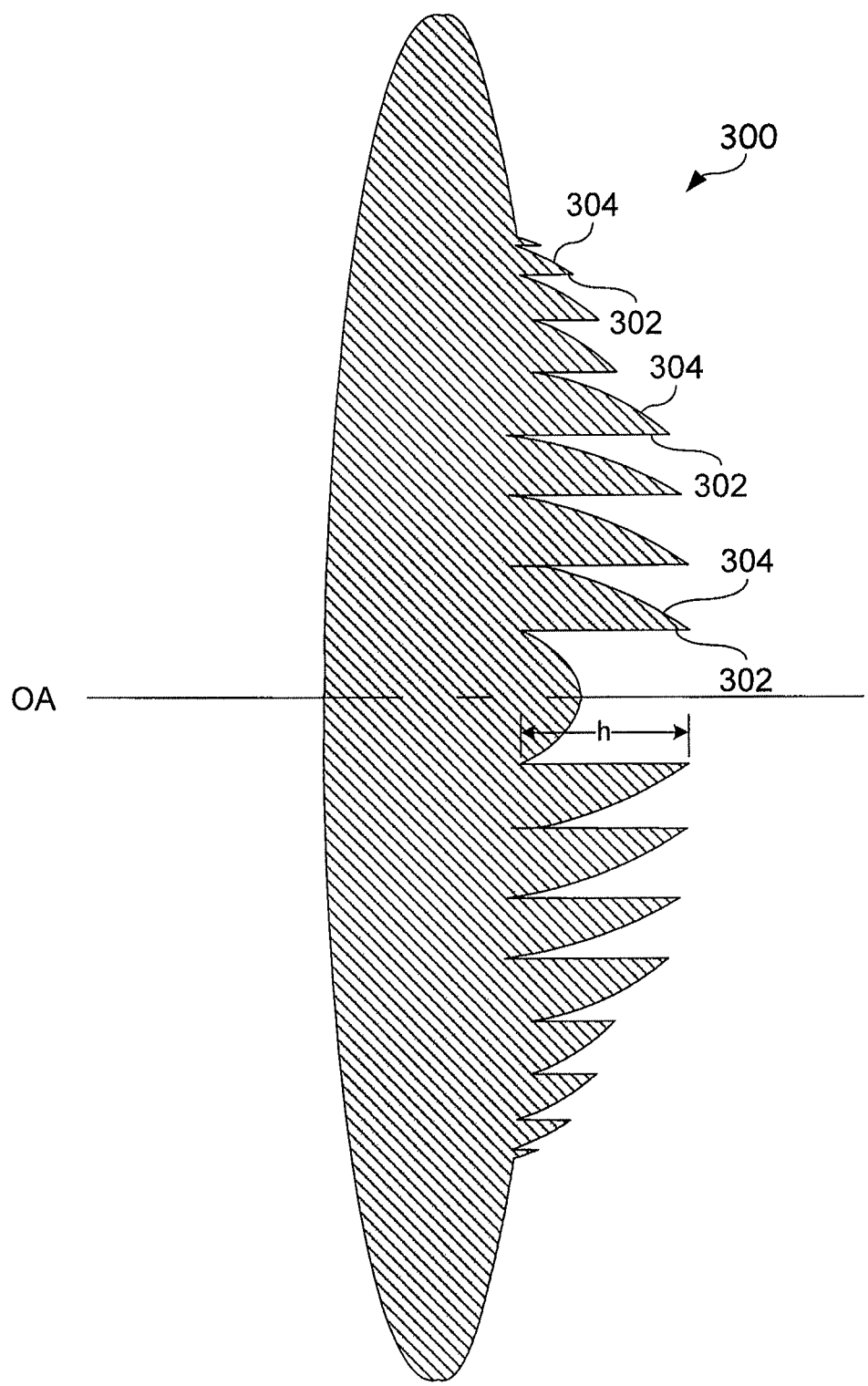
FIG. 3 provides a cross section 300 of a diffractive multifocal ophthalmic lens characterized by a plurality of annular zones depicts in accordance with embodiments of the present disclosure.

FIG. 3 provides a cross section 300 of a diffractive multifocal ophthalmic lens characterized by a plurality of annular zones depicts in accordance with embodiments of the present disclosure. Embodiments provides for phase-shifting between the plurality of annular zones to enhance the distance vision and maintain good intermediate vision. The amount of phase shift may be carefully optimized to have the constructive interference between the center-distance refractive region and the diffractive region. As the consequences, the distance vision is augmented and the intermediate vision is extended. In specifics, the initial phase of the center-distance region is adjusted to match the surrounding diffractive structure so that the constructive interference occurs at the distance focus and intermediate foci. Shifting initial phase upwards redistributes energy from near to intermediate and shifting downwards redistributes from distance to intermediate. A good balance is achieved in one embodiment when shifting initial phase to $\frac{1}{16}$ of a wave. This design maintains good distance, intermediate and near focus. Further optimization may result in other modified designs.

The process for determining these annular zones is described in U.S. Pat. No. 5,699,142 (Lee et al.), the entire contents of which are incorporated herein by reference. The boundary of each zone with respect to the optical axis is calculated. Steps 302 are placed at the radial zone boundaries between the various individual echelettes. Progressively reducing the step height of a selected group of individual echelettes 304 by a predetermined amount can reduce the unwanted effects of glare perceived as a halo or rings around a distant, discrete light source. The selected group of individual echelettes to be reduced in step height is all contained in what is termed an apodization zone.

Note that the step height of the echelettes 304 surrounding the optical axis (OA) remains constant over several echelettes 304 before beginning to reduce in size. Then, as the distance of each individual echelette from the optical axis OA increases the step height of each echelette 304 approaches zero. In other embodiments the height of the echelettes 304 surrounding the optical axis OA begins diminishing with the increase in the distance of the echelette 304 from the optical axis OA. These echettes may be further radially segmented as shown in FIG. 4.

Figure 4:
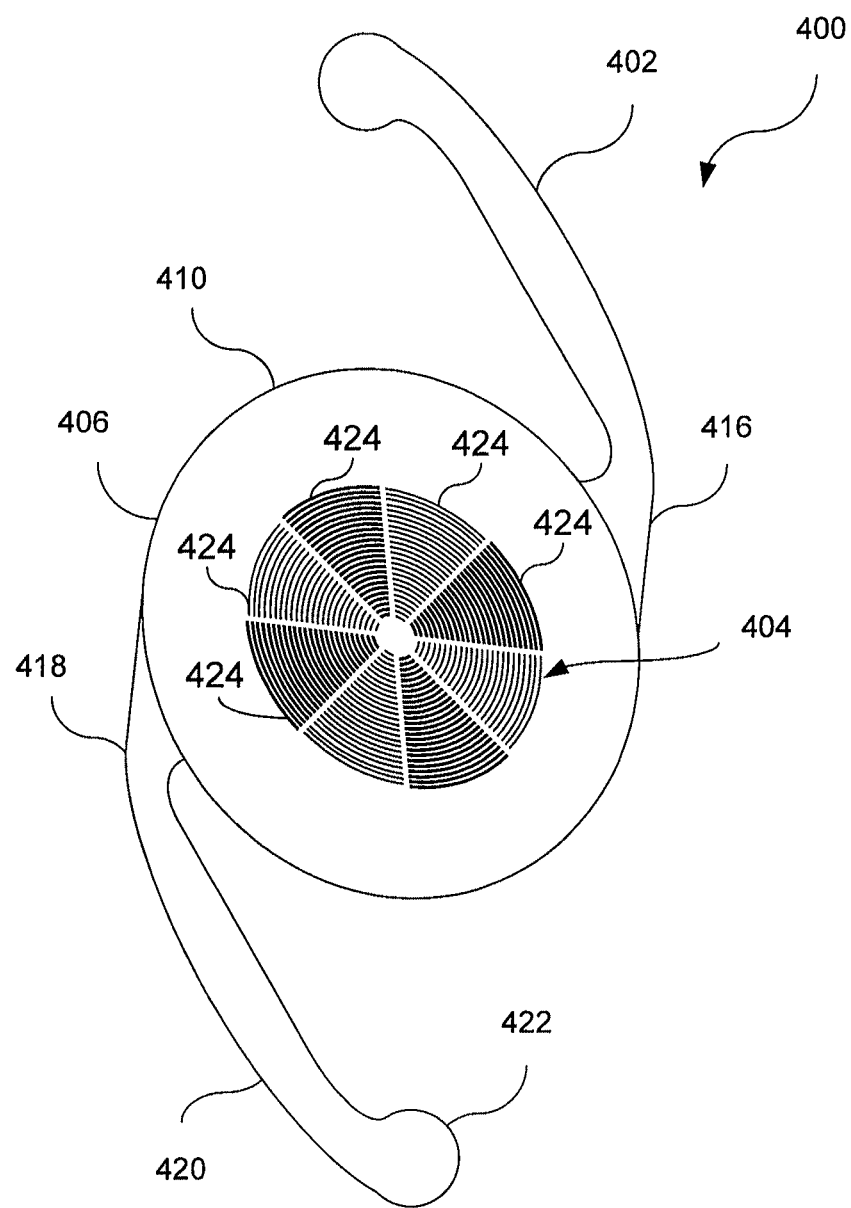
FIG. 4 provides a top down view of a radially segmented diffractive multifocal ophthalmic lens characterized by a plurality of annular zones depicts in accordance with embodiments of the present disclosure.

FIG. 4 provides a top down view of a radially segmented diffractive multifocal ophthalmic lens characterized by a plurality of annular zones depicts in accordance with embodiments of the present disclosure. radially segmented diffractive multifocal ophthalmic lens 400 includes haptics 402, which further include gusset 416, elbow 418 and distal portion 420 having widened portion 422; optic 410 which includes central radially apodized diffractive portion 404 having radially segmented zones 424 and a surrounding refractive area 406 In one embodiment thickness of elbow 418 and distal portion 420 of haptic 402 is uniform, and preferably between about 0.30 mm and 0.60 mm, with between about 0.40 mm and 0.50 mm being more preferred and about 0.43 being most preferred. Gusset 416, however, has a thickness that is reduced toward anterior side 212 of the optic. Gusset 416 preferably is between about 0.15 mm and 0.60 mm thick, with between about 0.25 mm and 0.35 mm thick being more preferred and about 0.30 mm being most preferred. This reduced thickness generally extends from edge 208 of the optic. The relatively thin cross section of gusset 416 and edge 308 provides a thinner profile when IOL 400 is inserted through the surgical incision. The reduced thickness of gusset 416 also facilitates fluid circulation (e.g., viscoelastic) between posterior side 214 and anterior side 212 of IOL. Alternatively, gusset 416 or optic 410 may be provided with other means (such as holes, grooves, notches, micro-fenestration, or protuberances (all not shown)) to facilitate fluid flow between posterior side 214 and anterior side 212 of the IOL. The relatively long length and radius of distal portion 420 provides greater contact with the capsular bag for better fixation when IOL 400 is implanted in the eye. Elbow 418 creates a hinge that allows haptic 402 to flex while minimizing buckling and vaulting of optic 410. Widened portion 422 increases the stiffness of haptic 402 just past elbow 418, thereby increasing the strength of haptic 402 at a critical stress point.

Embodiments of the present disclosure provide an improved apodized multi-focal design for an ocular implant, such as, intraocular lens (IOL) that utilizes a profile to provide improved distance vision for smaller pupils, such as photopic conditions, and improved near vision at larger pupils compared to previously available apodized diffractive multi-focal lenses.

Some patients need clearer distance vision at smaller pupil, that is, at photopic condition. Likewise, some patients require better vision at larger pupil, that is, at mesopic condition. For example, some patients have difficulty reading menus in restaurants with dim light where the pupil could be 4 mm or larger. Embodiments of the present disclosure utilize the energy distribution of a multi-focal design and are optimized to achieve higher energy for distance vision at 2.75 mm or smaller pupils. At the same time, it achieves higher energy for near vision compared to previously available ocular implants at 3.5 mm or larger pupil.

Embodiments also provide other features of an ocular implant of that include a thin edge for aiding in smaller incision during the implantation surgery; an about 5 to 10% or greater improvement in MTF values at 2 and 2.5 mm or smaller pupil as compare to previously available apodized multi-focal designs; and an about 15% or higher improvement in MTF values at 3.5 mm or larger pupil for near vision as compare to previously available apodized multi-focal designs. The 5 to 10% or greater improvement for smaller pupils allows for better distance vision at photopic conditions. Similarly the 15% improvement for larger pupils allows for improved near vision at mesopic or dim light condition. Embodiments of the present disclosure have demonstrated that one can reduce the energy to near, and use a larger lens region that directs light to near while providing good visual performance. Embodiments may optimize the area for design improvements that allow for better vision at all lighting conditions, such as, photopic and mesopic conditions for certain pupils. Visual disturbances will not be increased at night within some embodiments of the present disclosure.

Figure 5A:
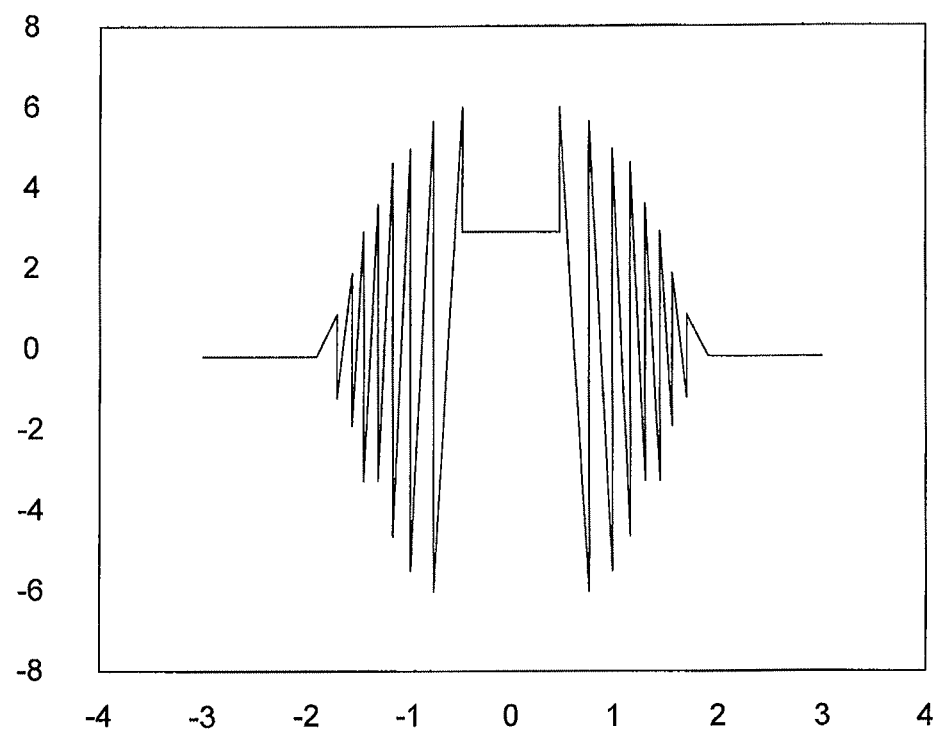
FIGS. 5A-5H provide graph depicting the results associated with shifting initial phase to redistribute energy between near, intermediate and distant for a 3 mm IOL in accordance embodiments of the present disclosure.
Figure 5B:
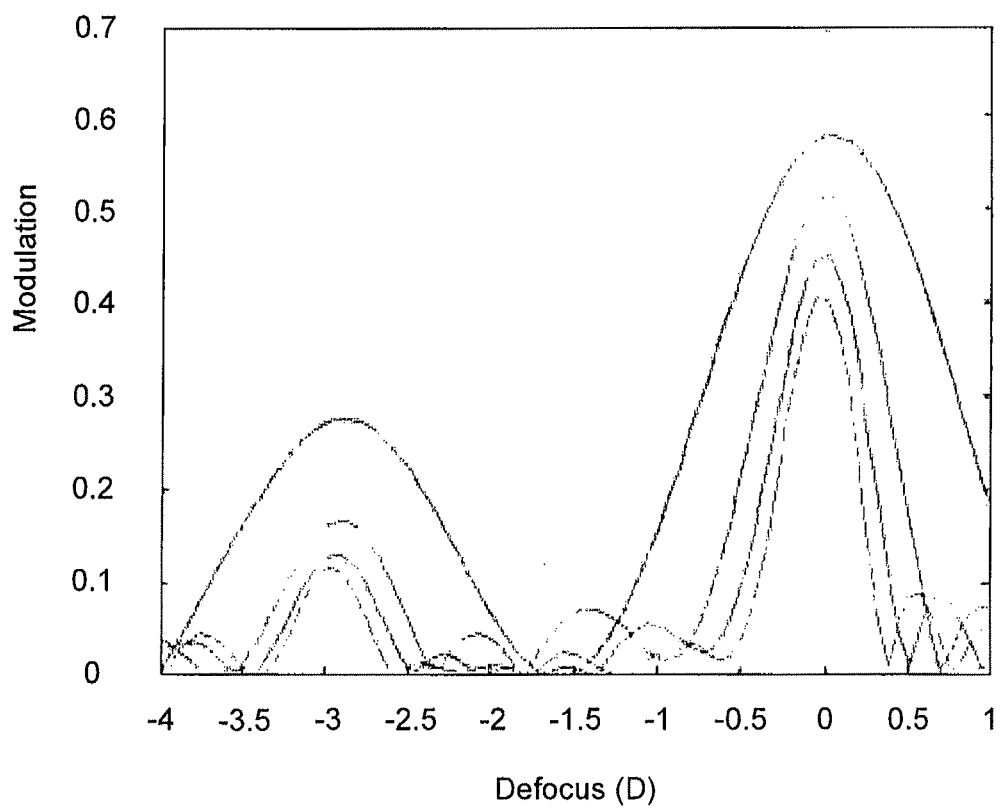
Figure 5C:
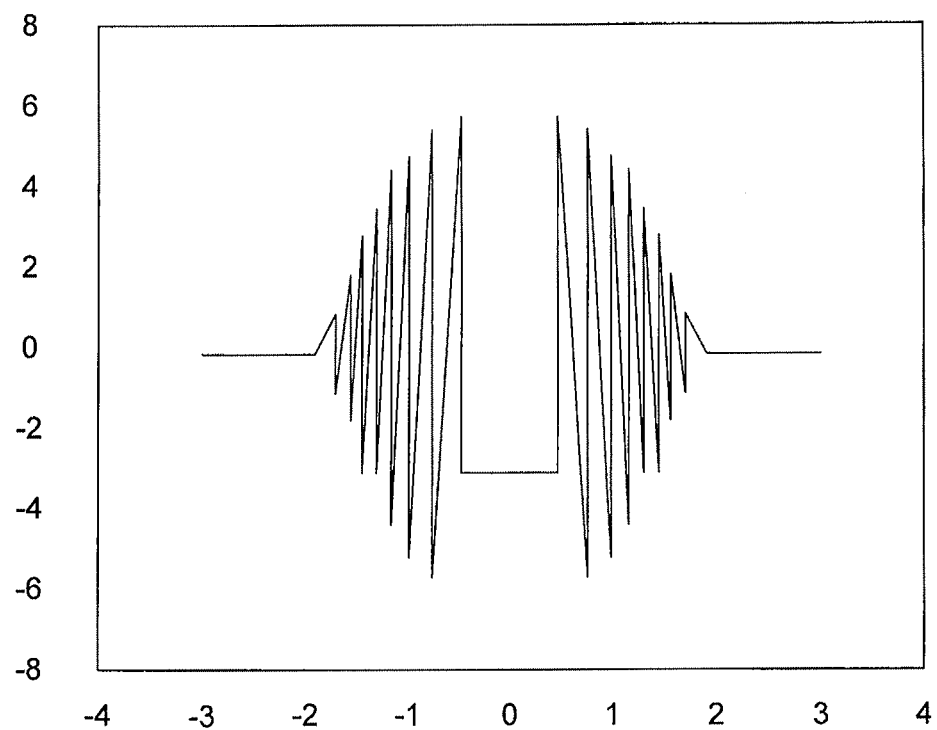
Figure 5D:
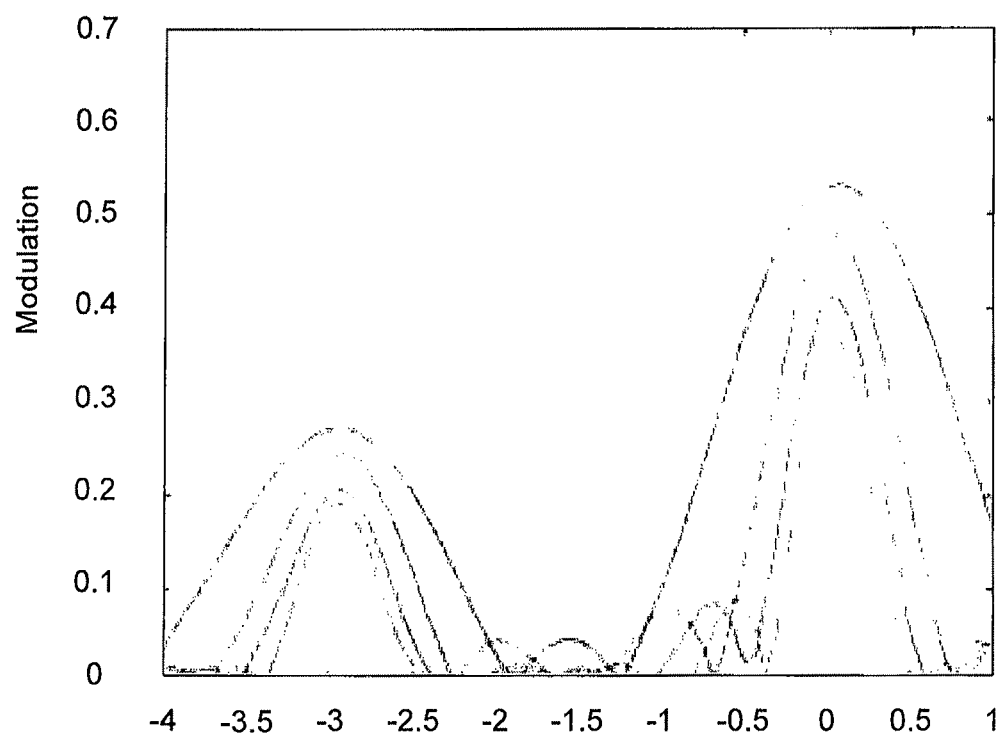
Figure 5E:
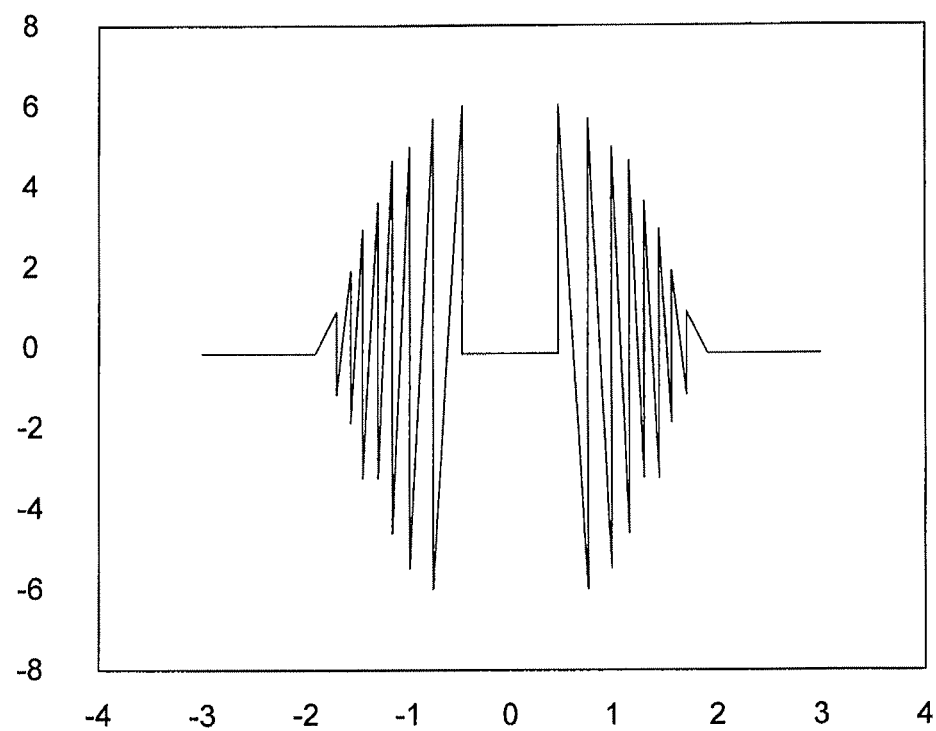
Figure 5F:
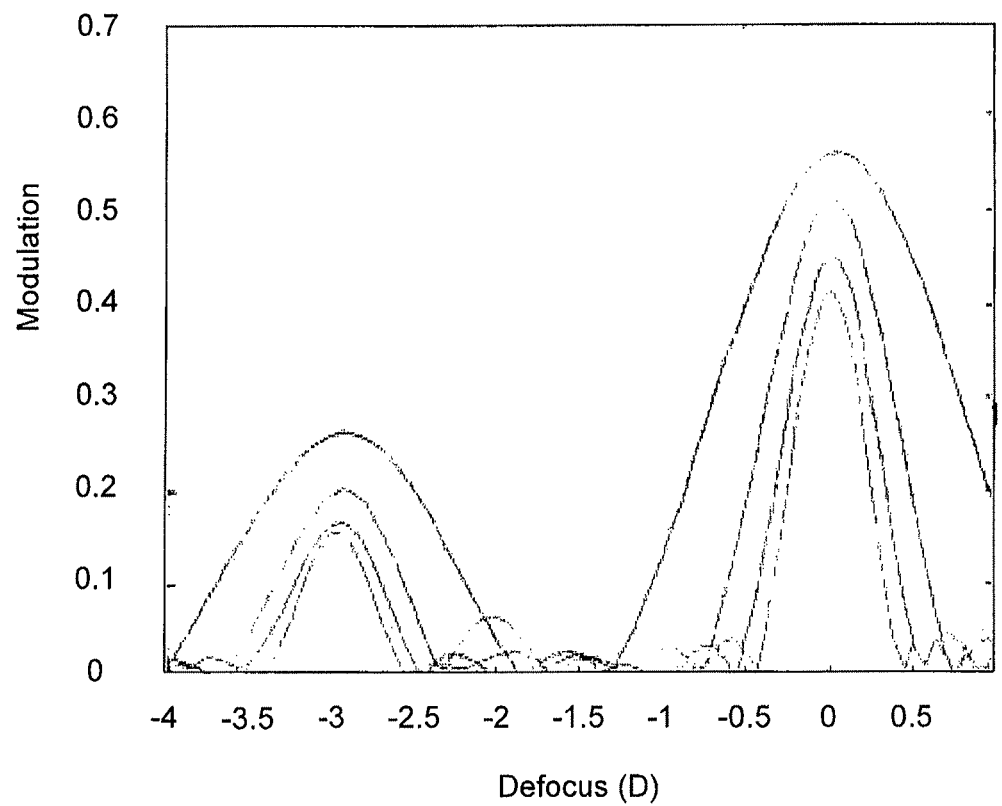
Figure 5G:
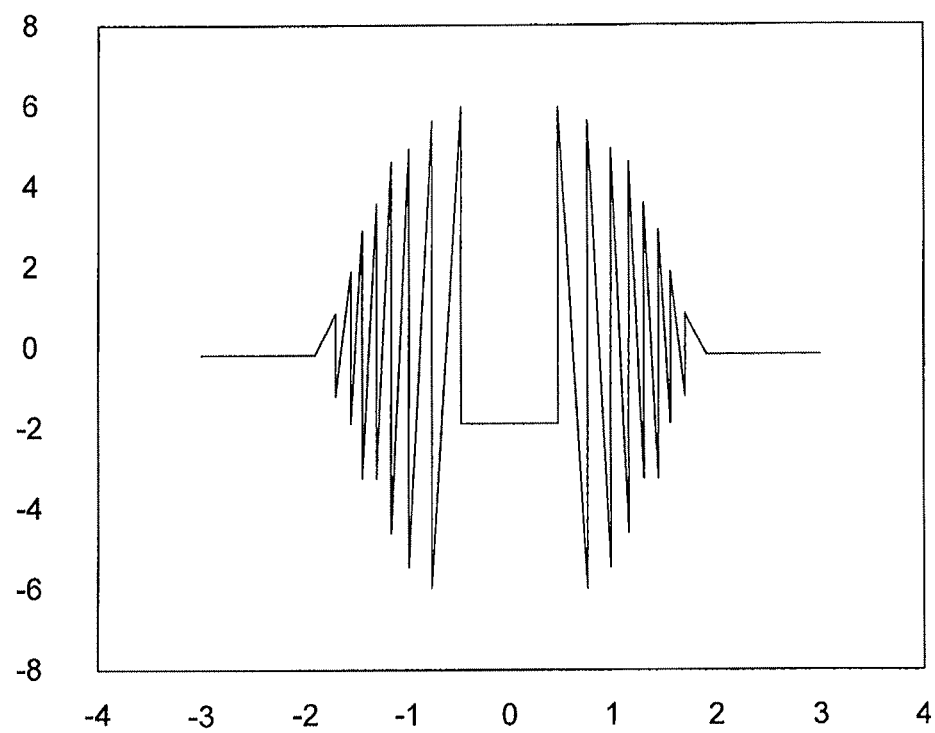
Figure 5H:
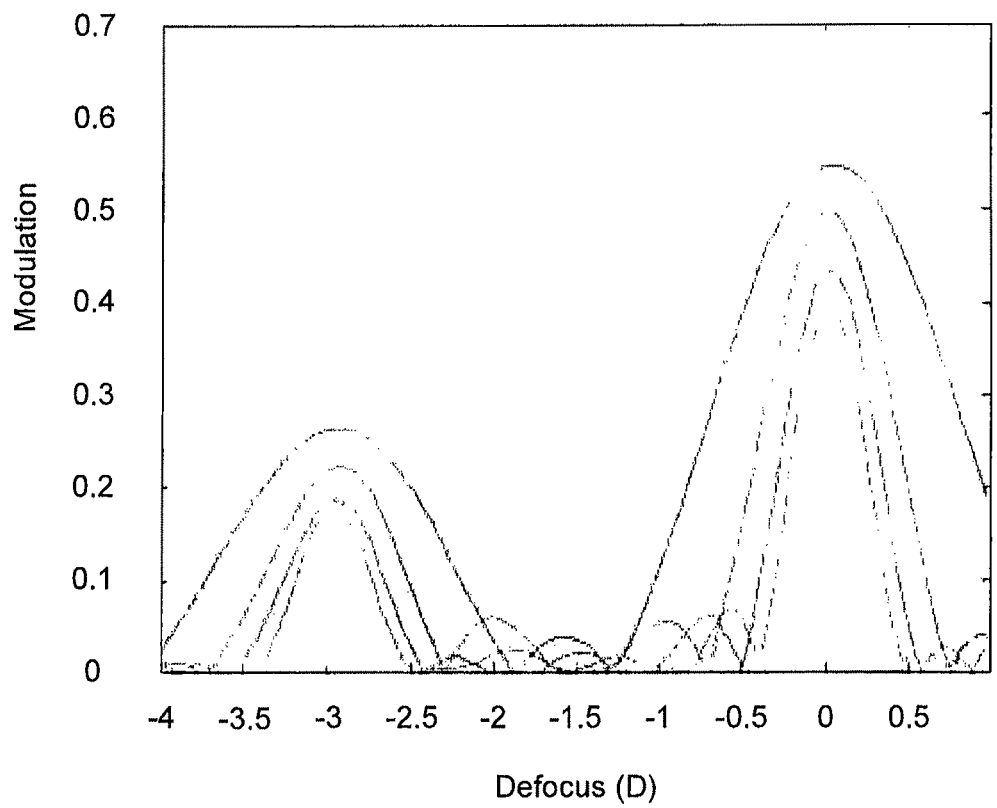

FIGS. 5A-5H provide graph depicting the results associated with shifting initial phase to redistribute energy between near, intermediate and distant for a 3 mm IOL in accordance embodiments of the present disclosure. Embodiments provides for phase-shifting within a combination of diffractive optics to enhance the distance vision and maintain good intermediate vision. The amount of phase shift may be carefully optimized to have the constructive interference between the center-distance refractive region and the diffractive region. As the consequences, the distance vision is augmented and the intermediate vision is extended. In specifics, the initial phase of the center-distance region is adjusted to match the surrounding diffractive structure so that the constructive interference occurs at the distance focus and intermediate foci. Shifting initial phase upwards redistributes energy from near to intermediate and shifting downwards redistributes from distance to intermediate. A good balance is achieved in one embodiment when shifting initial phase to $\frac{1}{16}$ of a wave. This design maintains good distance, intermediate and near focus. In FIGS. 5A and 5B the DD distance-center is shifted upwards by $\frac{1}{8}$ waves. In FIGS. 5C and 5D the DD distance-center is shifted downwards by $\frac{1}{8}$ waves. In FIGS. 5E and 5F the DD distance-center is unshifted. In FIGS. 5G and 5H the DD distance-center is shifted downwards by $\frac{1}{16}$ of a wave. Further optimization may result in other modified designs.

As shown in these FIGs., embodiments of the present disclosure may provide clearer distance vision at smaller pupil, that is, at photopic condition and better vision at larger pupil, that is, at mesopic conditions.

Figure 6:
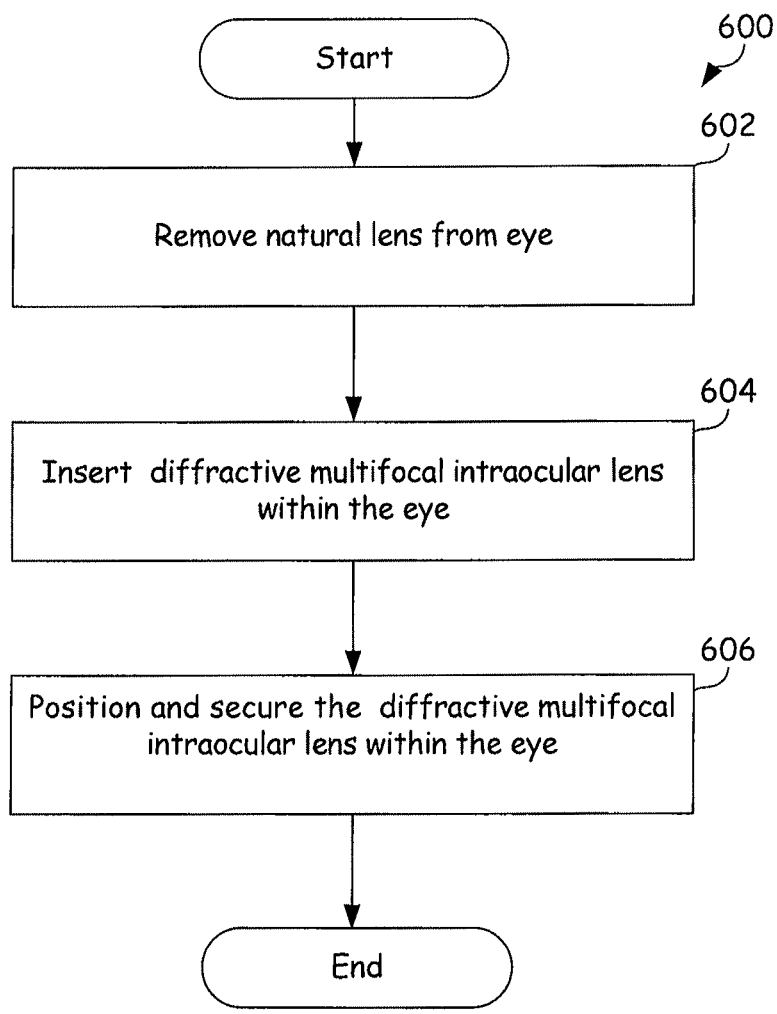
FIG. 6 provides a logic flow diagram of a method to correct for visual impairments such as aphakia of the eye.

FIG. 6 provides a logic flow diagram of a method to correct for visual impairments such as aphakia of the eye. Operations 600 begin with the removal of a natural lens from an eye in Step 602. An apodized diffractive multi-focal IOL may then be inserted within the eye. The lenses of the diffractive multi-focal IOL may be convex on both sides (bi-convex) and made of a soft plastic that can be folded prior to insertion. This folding allows placement through a reduced-size incision wherein the incision is smaller than the optic diameter of the diffractive multi-focal IOL. After surgical insertion into the eye in step 604 the IOL may gently unfold to restore vision. In Step 606, the IOL is positioned and secured within the eye. This may be done with the use of supporting arms (haptics) to provide for proper positioning of the IOL within the eye. Embodiments of the present disclosure may place or position the IOL in posterior chamber of the eye to replace the natural lens as shown in FIG. 1. This position allows the IOL to correct visual impairments such as the absence of a natural lens whether through disease or accident. The lens itself may be a diffractive multi-focal IOL as discussed previously. This allows patients with and without presbyopia who desire near intermediate and distant vision to experience independence from glasses following surgery such as cataract surgery.

In summary, embodiments of the present disclosure provide an improved diffractive multifocal design for ocular implant. This ocular implant includes a diffractive multifocal intraocular lens (IOL) and a number of haptics. The diffractive multifocal IOL passes optical energy in distance, intermediate and near conditions. The haptics mechanically couple to the diffractive multifocal IOL in order to position and secure the diffractive multifocal IOL within the eye. The diffractive multifocal IOL may include both a diffractive region and a refractive region. The diffractive region may be a central region or optic zone of the lens that includes concentric steps of gradually varying step heights in order to allocate energy based on lighting conditions and activity in order to create a full range of quality vision, i.e. near to distant or the patient. This allows conditions where the natural lens of the eye must be replaced to be corrected.

Other embodiments of the present disclosure provide a method to correct for visual impairment of aphakia. In one embodiment this involves removing a natural lens from an eye when the lens may be diseased or damaged through accident. Next a diffractive multifocal IOL may be inserted within the eye and then secured and positioned with a number of haptics. The diffractive region of the diffractive multifocal IOL may simultaneously pass optical energy to distant, intermediate and near focal points in bright optical conditions while the outer refractive region may pass optical energy to distance vision in dim optical conditions. Yet another embodiment of the present disclosure provides a method to correct visual impairment. This method involves passing optical energy to the retina wherein the optical energy may be imaged. This optical energy is passed with a diffractive multifocal IOL typically located within the eye and used to replace the natural lens. The diffractive multifocal IOL passes optical energy in distance, intermediate and near conditions. The diffractive multifocal IOL can have a central diffractive region and an outer refractive region.

Embodiments of the present disclosure allow patients having visual impairment to have clear distance vision at smaller pupil conditions, i.e. photopic conditions, and have improved vision at larger pupil, i.e. mesopic conditions.

As one of average skill in the art will appreciate, the term "substantially" or "approximately", as may be used herein, provides an industry-accepted tolerance to its corresponding term. As one of average skill in the art will further appreciate, the term "operably coupled", as may be used herein, includes direct coupling and indirect coupling via another component, element, circuit, or module. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship.

Although the present disclosure is described in detail, it should be understood that various changes, substitutions and alterations can be made hereto without departing from the spirit and scope of the disclosure as described by the appended claims.

What is claimed is:

1. An ocular implant, comprising:
a diffractive multifocal intraocular lens (IOL) operable to provide a distance, a near and an intermediate focus, the diffractive multifocal IOL having a thin edge operable to support a smaller incision, wherein the diffractive multifocal IOL comprises a bifocal diffractive region providing only the distance and near foci, a center-distance refractive region and an outer refractive region, the phase of the outer refractive region matching the phase of the bifocal diffractive region and the phase of the center-distance refractive region shifted out of phase from the bifocal diffractive region by between $1/8$ and $1/16$ of a wave to phase-shift optical energy such that constructive interference between the center-distance refractive region and the bifocal diffractive region occurs at both the distance and intermediate foci; and
a plurality of haptics coupled to the diffractive multifocal IOL operable to position the diffractive multifocal IOL within an eye.

2. The ocular implant of claim 1, wherein:
the diffractive region is operable to pass optical energy simultaneously to the distance, intermediate and near foci in bright optical conditions; and
the refractive region is operable to pass optical energy to distance vision in dim optical conditions.

3. The ocular implant of claim 1, wherein the diffractive multifocal IOL comprises a biconvex optic.

4. The ocular implant of claim 1, wherein the diffractive region comprises:
a plurality of concentric steps of varying step heights that allocate energy based on lighting conditions and activity to produce a full range (near to distant) of quality vision.

5. A method to correct visual impairment of aphakia comprising:
removing a natural lens from an eye;
inserting a diffractive multifocal intraocular lens (IOL) within the eye, the diffractive multifocal IOL operable to provide a near focus, an intermediate focus and a distance focus, the diffractive multifocal IOL comprises:
a center-distance refractive region,
a central bifocal diffractive region providing only the distance and near foci; and
an outer refractive region, the phase of the outer refractive region matching the phase of the central bifocal diffractive region to phase shift optical energy and the phase of the center-distance refractive region shifted out of phase from the bifocal diffractive region by between $1/8$ and $1/16$ of a wave such that constructive interference between the center-distance refractive region and the bifocal diffractive region occurs with the central bifocal diffractive region and the refractive region at both the intermediate and the distance foci;
positioning and securing the diffractive multifocal IOL within the eye with a plurality of haptics coupled to the diffractive multifocal IOL.

6. The method of claim 5, wherein the diffractive multifocal IOL comprises a biconvex optic.

7. The method of claim 5, wherein the central diffractive region comprises:
a plurality of concentric steps of varying step heights that allocate energy based on lighting conditions and activity to produce a full range (near to distant) of quality vision.

* * * * *